(12) United States Patent
Meyer et al.

(10) Patent No.: US 9,026,230 B2
(45) Date of Patent: May 5, 2015

(54) ELECTRODE PAD PACKAGING SYSTEMS AND METHODS

(71) Applicant: Covidien LP, Mansfield, MA (US)

(72) Inventors: Peter Meyer, Shrewsbury, MA (US); Lee Burnes, Wilbraham, MA (US); Scott R. Coggins, Littleton, MA (US); David Selvitelli, Suffield, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/088,659

(22) Filed: Nov. 25, 2013

(65) Prior Publication Data

US 2014/0216965 A1 Aug. 7, 2014

Related U.S. Application Data

(63) Continuation of application No. 13/559,632, filed on Jul. 27, 2012, now Pat. No. 8,594,812, which is a continuation of application No. 11/796,413, filed on Apr. 27, 2007, now Pat. No. 8,260,438.

(60) Provisional application No. 60/795,382, filed on Apr. 27, 2006.

(51) Int. Cl.
*A61B 1/00* (2006.01)
*A61N 1/04* (2006.01)

(52) U.S. Cl.
CPC .............. *A61N 1/046* (2013.01); *A61N 1/0472* (2013.01); *A61N 1/048* (2013.01); *A61N 1/0488* (2013.01); *A61N 1/0492* (2013.01)

(58) Field of Classification Search
USPC ......................................... 607/152
See application file for complete search history.

(56) References Cited

U.S. PATENT DOCUMENTS

| | | |
|---|---|---|
| 3,685,645 A | 8/1972 | Kawaguchi |
| 3,808,981 A | 5/1974 | Shaw |
| 3,990,683 A | 11/1976 | Ravreby |
| 4,583,643 A | 4/1986 | Sanderson |
| 4,989,607 A | 2/1991 | Keusch et al. |
| 5,148,805 A | 9/1992 | Scharnberg |
| 5,163,554 A | 11/1992 | Lampropoulos et al. |
| 5,356,428 A | 10/1994 | Way |
| 5,366,497 A | 11/1994 | Ilvento et al. |
| 5,402,884 A | 4/1995 | Gilman et al. |
| 5,462,157 A | 10/1995 | Freeman et al. |
| 5,579,919 A | 12/1996 | Gilman et al. |
| 5,645,571 A | 7/1997 | Olson et al. |
| 5,697,955 A | 12/1997 | Stolte |
| 5,700,281 A | 12/1997 | Brewer et al. |
| 5,817,151 A | 10/1998 | Olson et al. |
| 5,827,184 A | 10/1998 | Netherly et al. |
| 5,850,920 A | 12/1998 | Gilman et al. |
| 5,951,598 A | 9/1999 | Bishay et al. |
| 5,984,102 A | 11/1999 | Tay |
| 6,048,640 A | 4/2000 | Walters et al. |
| 6,205,361 B1 | 3/2001 | Kuzma et al. |
| 6,251,489 B1 | 6/2001 | Weiss et al. |
| 6,272,385 B1 | 8/2001 | Bishay et al. |
| 6,289,896 B1 | 9/2001 | Hart |
| 6,336,047 B1 | 1/2002 | Thu et al. |

(Continued)

*Primary Examiner* — Robert N Wieland
(74) *Attorney, Agent, or Firm* — Lisa E. Winsor, Esq.

(57) ABSTRACT

An electrode pad packaging system including an electrode pouch, an electrode pad (e.g., a defibrillation electrode pad) and a sacrificial source of moisture is disclosed. The electrode pad and the sacrificial source of moisture are each disposed at least partially within the electrode pouch.

20 Claims, 11 Drawing Sheets

(56) References Cited

U.S. PATENT DOCUMENTS

| | | |
|---|---|---|
| 6,393,670 B1 | 5/2002 | Bealmear |
| 6,603,318 B2 | 8/2003 | Hansen et al. |
| 6,611,709 B2 | 8/2003 | Faller et al. |
| 6,662,056 B2 | 12/2003 | Picardo et al. |
| 6,675,057 B2 | 1/2004 | Liu |
| 6,714,824 B1 | 3/2004 | Ohta et al. |
| 6,782,293 B2 | 8/2004 | Dupelle et al. |
| 6,792,301 B2 | 9/2004 | Munro et al. |
| 6,850,920 B2 | 2/2005 | Vetter |
| 6,874,621 B2 | 4/2005 | Solosko et al. |
| 6,933,395 B1 | 8/2005 | Mohr et al. |
| 6,935,889 B2 | 8/2005 | Picardo et al. |
| 7,016,727 B2 | 3/2006 | Powers et al. |
| RE39,250 E | 8/2006 | Freeman et al. |
| 2001/0023001 A1 | 9/2001 | Weiss et al. |
| 2003/0083729 A1 | 5/2003 | Solosko et al. |
| 2005/0011780 A1 | 1/2005 | Simon et al. |
| 2005/0129812 A1 | 6/2005 | Brown et al. |
| 2006/0040803 A1 | 2/2006 | Perez, Jr. |
| 2006/0142831 A1 | 6/2006 | Nova et al. |
| 2008/0210592 A1* | 9/2008 | Anderson et al. ............ 206/701 |
| 2012/0290061 A1 | 11/2012 | Meyer et al. |

\* cited by examiner

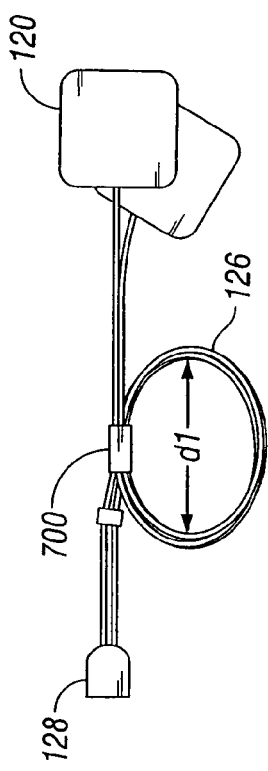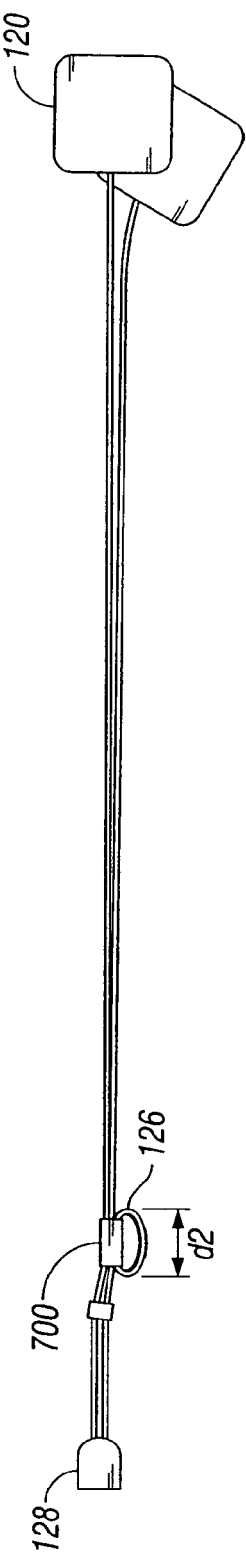
FIG. 7A
FIG. 7B
FIG. 7C
FIG. 7D

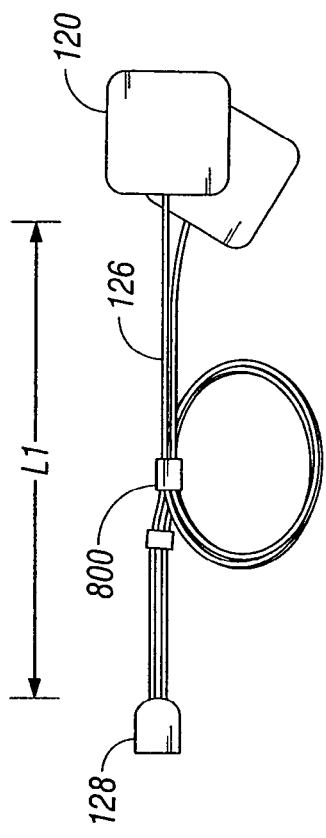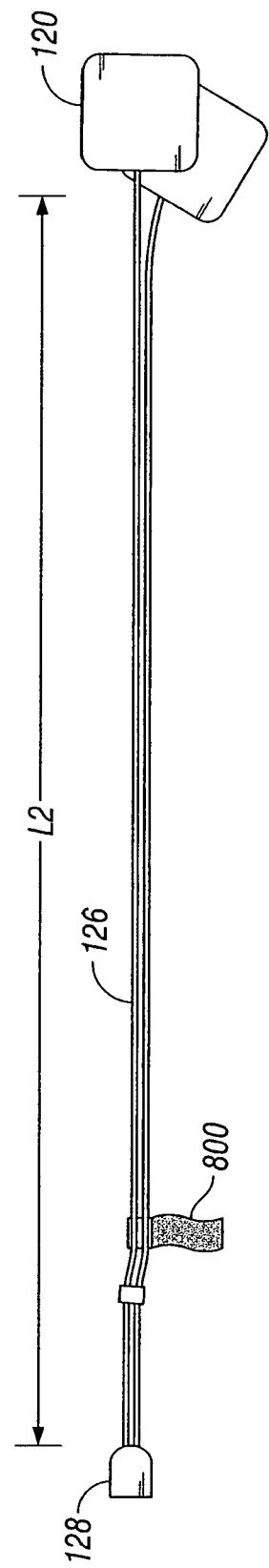

ELECTRODE PAD PACKAGING SYSTEMS AND METHODS

CROSS REFERENCE TO RELATED APPLICATION

This application is a continuation of and claims the benefit of U.S. patent application Ser. No. 13/559,632 filed Jul. 27, 2012, which claims the benefit of U.S. patent application Ser. No. 11/796,413 filed Apr. 27, 2007, now U.S. Pat. No. 8,260,438, which claims the benefit and priority of U.S. Provisional Patent Application No. 60/795,382 filed on Apr. 27, 2006 and titled METHODS OF CONSTRUCTING PACKAGING ELECTRODES. The above-identified applications are each hereby incorporated herein by reference in their entireties.

BACKGROUND

The present disclosure relates to packages for electrodes. Several methods and packages are disclosed for packaging electrodes, such as disposable defibrillation electrodes. Generally, the disclosed methods and packages facilitate the connection of defibrillation electrodes to a defibrillator prior to the electrodes being used on a patient, while allowing the electrodes to maintain a sufficient amount of moisture to be able to properly function.

Electrodes which are typically used in medical applications generally include a conductor and a connector. The connector is attached at one end to the conductor and includes a plug at the other end to be plugged into a defibrillator or other device. The conductor is often covered or coated in a conductive gel, which enhances its ability to adhere to a patient's skin. When the conductive gel becomes too dry, it may lose its ability to adhere to a patient or demonstrate excessively high contact impedance. To prevent the conductive gel from drying out, the electrode may be stored in a package prior to use.

In a medical setting, there are often a variety of different defibrillators and electrodes at a clinician's disposal and it is not uncommon for several of the defibrillators and electrodes to have different manufacturers. Compatibility among defibrillators (or other medical devices) and electrodes of different brands is often lacking, which can cause confusion as to which particular electrode to use with a given defibrillator. Thus, clinicians open electrode packages to determine if the electrode (or electrode plug) is compatible with the defibrillator (i.e., does the electrode plug fit into the receptacle on the defibrillator?). As can be appreciated, testing electrodes in this fashion leads to waste, as the electrodes that are not compatible are likely to become too dry if not used in a timely fashion.

Further, in preparation for an emergency situation, clinicians may perform as many steps as possible before such an emergency situation arises. For example, a clinician may prepare a defibrillator by "pre-connecting" a compatible electrode to the defibrillator. Pre-connecting a compatible electrode to a defibrillator when able to prevent rapid diffusion of moisture from the conductive gel reduces the number of steps that need to take place during an actual emergency.

SUMMARY

The present disclosure relates to an electrode pad packaging system including an electrode pouch, an electrode pad (e.g., a defibrillation electrode pad) and a sacrificial source of moisture. The electrode pad and the sacrificial source of moisture are each disposed at least partially within the electrode pouch.

In disclosed embodiments, the sacrificial source of moisture includes a gel or a solid hydrogel. Further, the sacrificial source of moisture may be attached to an interior surface of the electrode pouch.

According to disclosed embodiments, the electrode pouch may be gas permeable or gas impermeable. Additionally, the electrode pouch may be openable and re-sealable.

In a disclosed embodiment, a conductive gel is disposed on at least a portion of the electrode pad and a cover is disposed adjacent the conductive gel.

The present disclosure also relates to a method of packaging an electrode pad, including providing an electrode pouch, providing an electrode pad (e.g., a defibrillation electrode pad) and providing a sacrificial source of moisture. The electrode pad and the sacrificial source of moisture are configured to be placed at least partially within the electrode pouch.

In embodiments related to this method, the sacrificial source of moisture includes a gel or a solid hydrogel and may be attached to an interior surface of the electrode pouch.

According to disclosed embodiments related to this method, the electrode pouch may be gas permeable or gas impermeable. Additionally, the electrode pouch may be openable and re-sealable. Additionally, a conductive gel is disposed on at least a portion of the electrode pad in a disclosed embodiment.

The present disclosure also relates to a defibrillation electrode package including an electrode pouch and a sacrificial source of moisture. The sacrificial source of moisture includes a gel that is configured to diffuse within the electrode pouch. In an embodiment, the sacrificial source of moisture is attached to an interior surface of the electrode pouch.

BRIEF DESCRIPTION OF THE DRAWINGS

Various embodiments of electrode packages are described herein with reference to the drawings wherein:

FIG. 7A is a side view of a first embodiment of extensible electrode lead wires including a tube in accordance with the present disclosure illustrated with lead wires in a non-extended manner;

FIG. 7B is a side view of the extensible lead wires of FIG. 7A illustrated in an extended manner;

FIGS. 7C and 7D are cross-sectional views of embodiments of the tube of FIGS. 7A and 7B;

FIG. 8A is a side view of a second embodiment of extensible electrode lead wires including a strap in accordance with the present disclosure illustrated with lead wires in a non-extended manner;

FIG. 8B is a side view of the extensible lead wires of FIG. 8A illustrated in an extended manner;

DETAILED DESCRIPTION

Figure 1A:
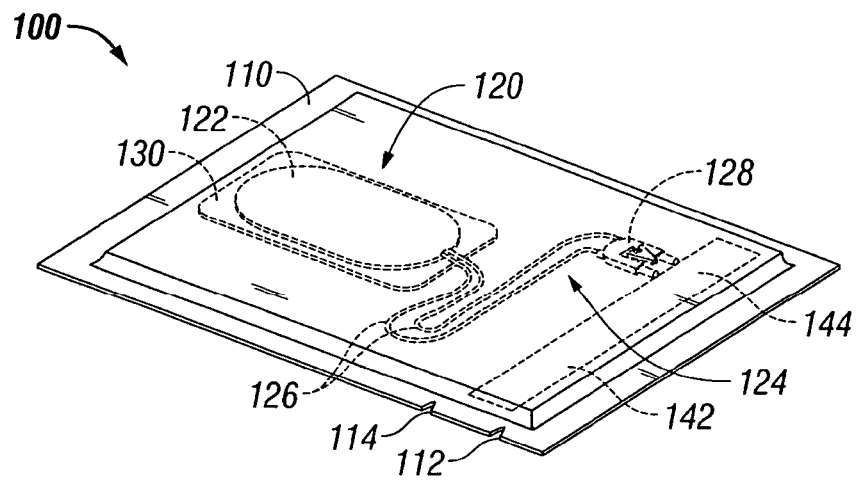
FIG. 1A is a perspective view of a first embodiment of an electrode package in accordance with the present disclosure.

Embodiments of the presently disclosed electrode packages will now be described in detail with reference to the drawing figures wherein like reference numerals identify similar or identical elements.

Figure 1B:
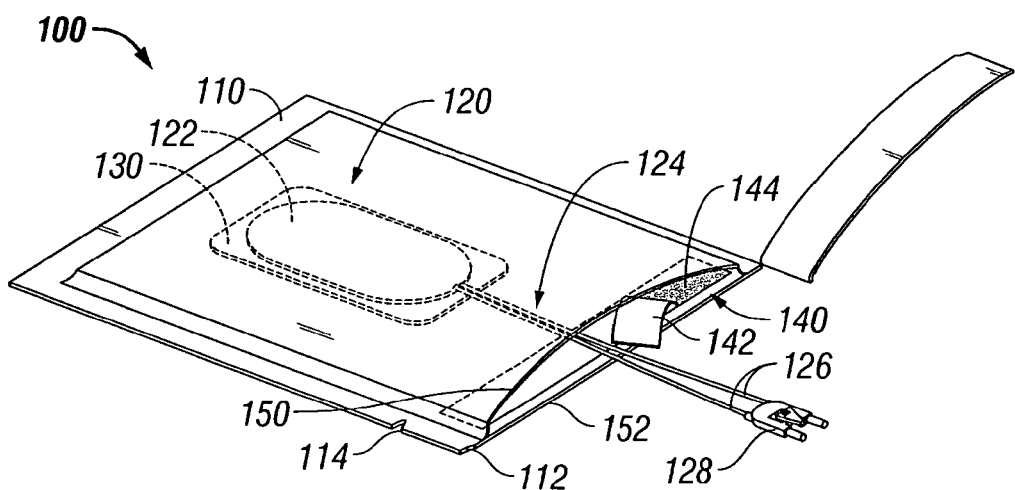
FIG. 1B is a perspective view of the electrode package of FIG. 1A, wherein the electrode package is partially open.
Figure 1C:
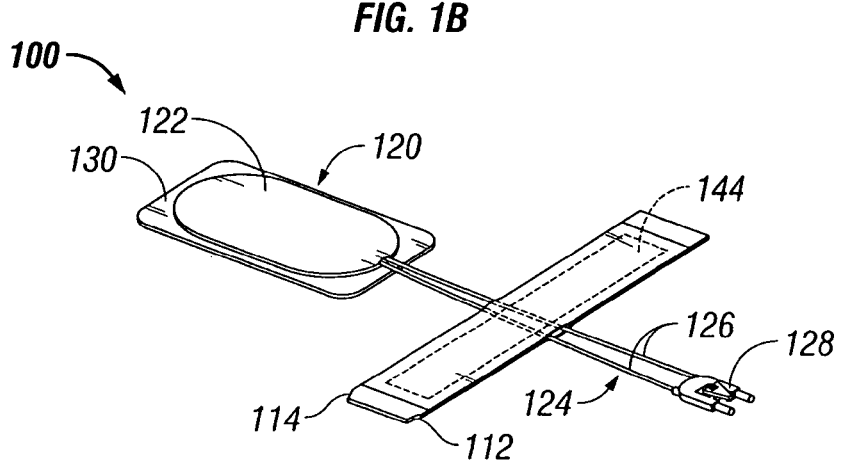
FIG. 1C is a perspective view of the electrode package of FIGS. 1A-1B, wherein the electrode package is fully open and the electrode is revealed.

A first embodiment of an electrode package in accordance with the present disclosure is generally referenced in FIGS. 1A-1C by reference numeral 100. As will be described with reference to FIGS. 1A-1C, the electrode package 100 generally includes an electrode pouch 110 which encloses at least one electrode 120.

The electrode 120 includes an electrode pad 122 and an electrode connector 124. The electrode pad 122 is generally made of a conductive material and is adhered to a patient during a medical procedure. The electrode connector 124 connects the electrode pad 122 to a medical device, such as a defibrillator (not shown). The electrode connector 124 includes lead wires 126 which electrically connect the electrode pad 122 to a plug portion 128. Additionally, a conductive gel (not shown) at least partially covers the electrode pad 122 and is protected by a cover 130. The cover may be any suitable sheet adhered to the electrode pad 122 via the conductive gel. One possible sheet material is silicone-coated mylar. Other materials are also contemplated.

The electrode pouch 110 functions to maintain a sufficient amount of moisture therewithin to help prevent the conductive gel from becoming too dry. The electrode pouch 110 may be generally gas-impermeable. Over time, however, the conductive gel will naturally lose at least a portion of its moisture content. A conductive pad 122 where the conductive gel is too dry is not optimal for medical use at least because conductive pad 122 may lose its ability to adhere to a patient or demonstrate excessively high contact impedance.

To determine if the conductive pad 122 is compatible with a particular defibrillator, for example, a clinician may attempt to plug the electrode 120 into the defibrillator. In this embodiment, a user can tear the electrode pouch 110 open at a first notch 112 to expose its contents, particularly plug portion 128 (see FIG. 1B). A score line (not shown) may be formed in electrode pouch 110 in line with the first notch 112 to facilitate opening of the pouch 110.

At this point the electrode 120 may be tested for compatibility with a defibrillator. An example of when the particular conductive pad 122 is not compatible is when the plug portion 128 is found to be incompatible with a receptacle of the defibrillator. If the conductive pad 122 is determined to be compatible and thus usable, the clinician may opt to use the electrode 120 in a timely manner or he may opt not to use it right away. If he desires to use the electrode 120 soon after the time he tests it, the clinician can remove the electrode 120 from the electrode pouch 110 and proceed to use it. If, however, he would not like to use the electrode 120 right away, he can place the lead wires 126 and plug portion 128 back into the electrode pouch 110 and reseal the electrode pouch 110 to help maintain the sufficient moisture content of the conductive gel.

In the embodiment illustrated in FIGS. 1A-1C, to reseal the electrode pouch 110, a closure element 140 is used. FIG. 1B illustrates a closure element 140 which includes a release liner 142 and an adhesive strip 144. To reveal the adhesive strip 144, the release liner 142 is removed (e.g., peeled off). FIG. 1B illustrates the release liner 142 partially peeled off the adhesive strip 144. The electrode pouch 110 may then be resealed by compressing a top portion 150 of the electrode pouch 110 with a bottom portion 152 of the electrode pouch 110. Thus, gas is capable of entering the electrode pouch 110 during the time between the initial opening of the electrode pouch 110 and when the electrode pouch 110 is resealed. Alternatively, the release liner 142 may be affixed to the upper portion 150 (or lower portion 152) of the electrode pouch 110, such that when the electrode pouch 110 is opened, the release liner 142 is automatically removed. Further, other types of closure elements 140 may be used, such as a mechanical sealing means (e.g., a Zip-Loc™-type of seal).

Referring now to FIG. 1C, to remove the electrode 120 from the resealed electrode pouch 110, the electrode pouch 110 can be re-opened by tearing it along a second notch 114 and accompanying score line (not shown), for example. The portion of the electrode pouch 110 between the first notch 112 and the second notch 114 may adhere to the lead wires 126. If desired, this portion can be cut off to remove the excess material. The electrode 120 is then ready to be adhered to a patient.

A second embodiment of the electrode package in accordance with the present disclosure is generally referenced in FIGS. 2A-2D by reference numeral 200. The electrode package 200 of this embodiment generally includes an electrode pouch 202, an electrode 220 and a grommet 240.

The electrode pouch 202 generally includes a first compartment 204, a second compartment 206 and a channel 208 interconnecting the first and second compartments 204, 206. The electrode 220 generally includes an electrode pad 222 and an electrode connector 224, including lead wires 226 and a plug portion 228. The plug portion 228 enables the electrode 220 to be plugged into a medical device, such as a defibrillator (not shown). Additionally, conductive gel (not shown) at least partially covers the electrode pad 222 and is protected by a cover 232.

Figure 2A:
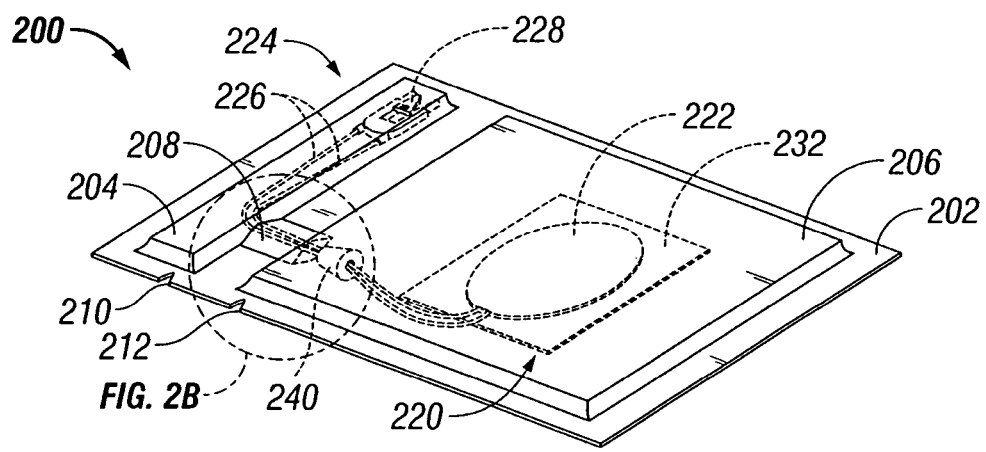
FIG. 2A is a perspective view of a second embodiment of an electrode package in accordance with the present disclosure.
Figure 2B:
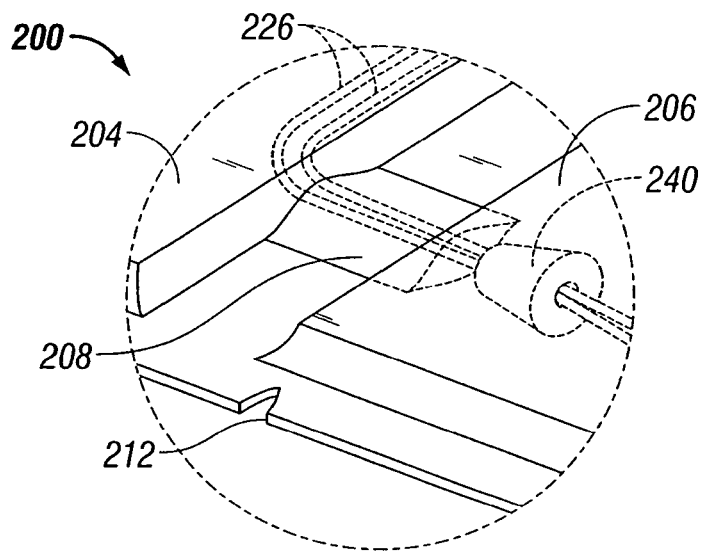
FIG. 2B is an enlarged perspective view the portion of the second embodiment of the electrode package indicated in FIG. 2A.

The electrode pouch 202 may be formed of two sheets of material which may be sealed at or near their perimeters to form a generally gas-impermeable electrode pouch. Referring to FIG. 2A, the first compartment 204 of the electrode pouch 202 houses the plug portion 228 and a segment of the lead wires 226 and the second compartment 206 of the electrode pouch 202 houses the electrode 220, a segment of the lead wires 226 and the grommet 240 which is connected to a portion of the lead wires 226. Alternatively, the grommet 240 may allow the lead wires 226 to pass therethrough. The channel 210, as best illustrated in FIG. 2B, spans the gap between the first compartment 204 and the second compartment 206 and allows a portion of the lead wires 226 to travel therethrough.

Figure 2C:
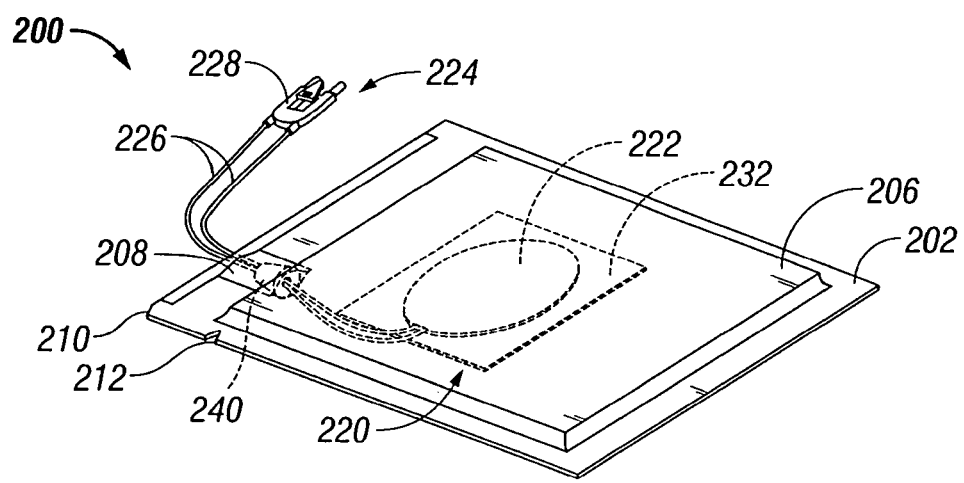
FIG. 2C is a perspective view of the electrode package of FIG. 2A, wherein the electrode package is partially open.

In use, to remove the plug portion 228 and a segment of the lead wires 226 from the first compartment 204, the electrode pouch 202 may be torn at a first notch 210. As illustrated in FIG. 2C, this exposes a segment of the lead wires 226 and the plug portion 228, which can then be plugged into a medical device for testing and/or for use.

If a clinician is not ready to use the electrode 220, he may then pull the segment of the lead wires 226 away from the channel 208, thus causing the grommet 240 to become wedged into the channel 208 (as illustrated in FIG. 2C). It is envisioned for the channel 208 and the grommet 240 to be shaped and sized such that the grommet 240 restricts air flow from the ambient air into the second compartment 206, thus keeping the moisture level within the second compartment 206, and more specifically, the moisture level of the conductive gel, at a desirable level.

Figure 2D:
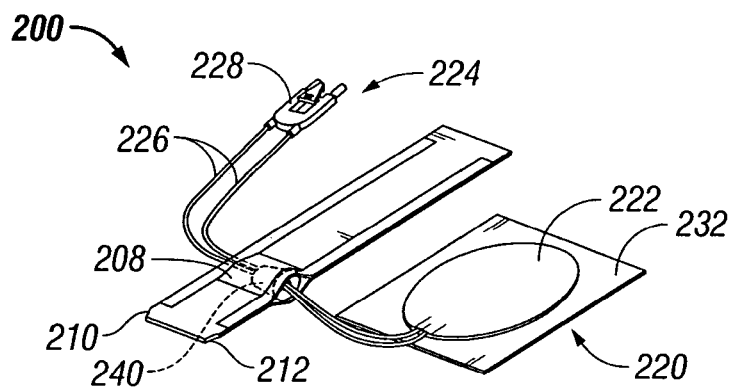
FIG. 2D is a perspective view of the electrode package of FIGS. 2A and 2C, wherein the electrode is revealed.

With particular reference to FIG. 2D, when the clinician is ready to use the electrode 220, he may tear the electrode pouch 202 at a second notch 212. This tearing of the electrode pouch 202 for the second time will expose the electrode pad 222. To place the electrode pad 222 onto a patient, its cover 230 is peeled off to reveal conductive gel (not shown). The electrode pad 222 may then be adhered to a portion of a patient and the plug portion 228 may be plugged into a medical device. In this embodiment, it is envisioned for the plug portion 228 and the segment of the lead wires 226 that were housed in the first compartment 204 to be pushed or pulled through the channel 208 toward the electrode pad 222. This may result in the electrode 220 and the electrode pouch 202 being completely separated.

Figure 3:
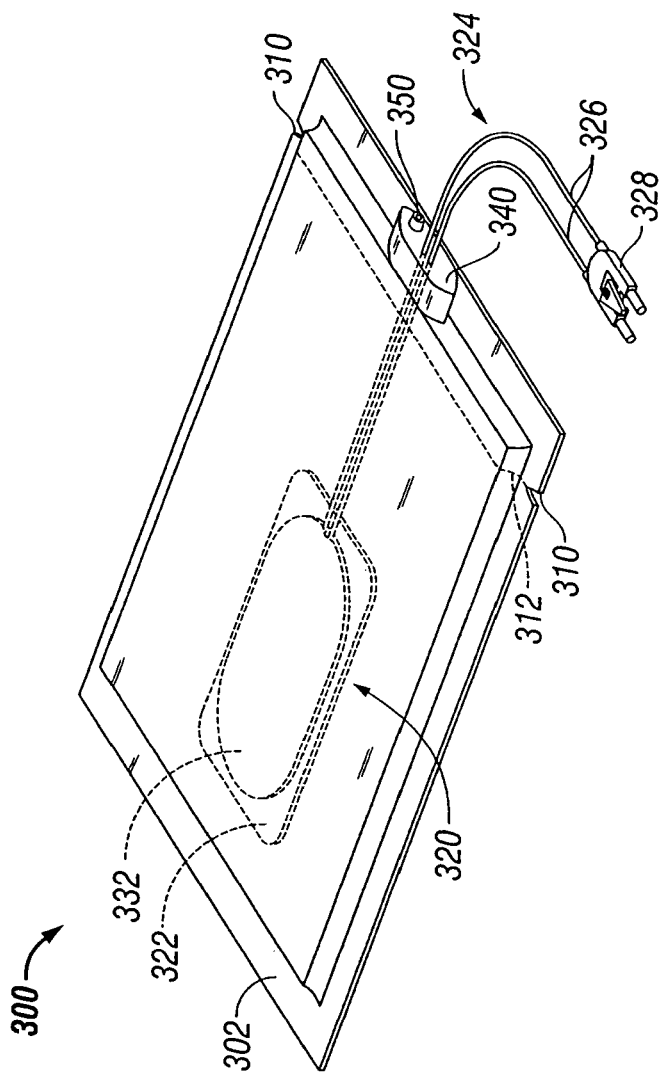
FIG. 3 is a perspective view of a third embodiment of an electrode package in accordance with the present disclosure.

A third embodiment of the electrode package in accordance with the present disclosure is generally referenced in FIG. 3 by reference numeral 300. The electrode package 300 of this embodiment generally includes an electrode pouch 302, an electrode 320 and a shell 340.

The electrode pouch 302 is formed of two sheets of generally gas impermeable material. The electrode 320 generally includes an electrode pad 322 and an electrode connector 324, which includes lead wires 326 and a plug portion 328. The plug portion 328 enables the electrode 320 to be plugged into a medical device, such as a defibrillator (not shown). Additionally, conductive gel (not shown) at least partially covers the electrode pad 322 and is protected by a cover 332.

The material comprising the electrode pouch 302 is sealed around its perimeter. The shell 340 may be formed on the electrode pouch 302 and may attach to the lead wires 326 to enable them to pass from the inside of the electrode pouch 302 to its exterior. Additionally, a check valve 350 is located on the shell 340.

The check valve 350 is a one-way valve which permits air to escape the interior of the electrode pouch 302, while preventing outside air from entering the electrode pouch 302. Any check valve suitable for this intended use is contemplated. Thus, the electrode pouch 302 is not gas impermeable. As can be appreciated, this arrangement allows excess air to be dispensed from the electrode pouch 302 after the electrode pouch 302 is sealed. Therefore, the size of the package may be reduced and the possibility of the electrode pouch 302 becoming ruptured is also reduced.

Notwithstanding the one-way gas permeability, the electrode pouch 302 of this embodiment maintains the moisture of the conductive gel for a sufficiently long period of time. The relative humidity of the interior of the electrode pouch 302 will remain near 100%, thus preventing rapid diffusion of moisture from the conductive gel to the interior of the electrode pouch 302.

To remove the electrode 320 from the electrode pouch 302, one may tear open the electrode pouch 302 along a notch 310 (two notches 310 are shown). There may also be a perforated line 312 disposed on the electrode pouch 302 adjacent the notch(es) 310 to facilitate opening the electrode pouch 302. Once the electrode pouch 302 is open, the electrode 320 may be removed from the interior of the electrode pouch 302.

Figure 3A:
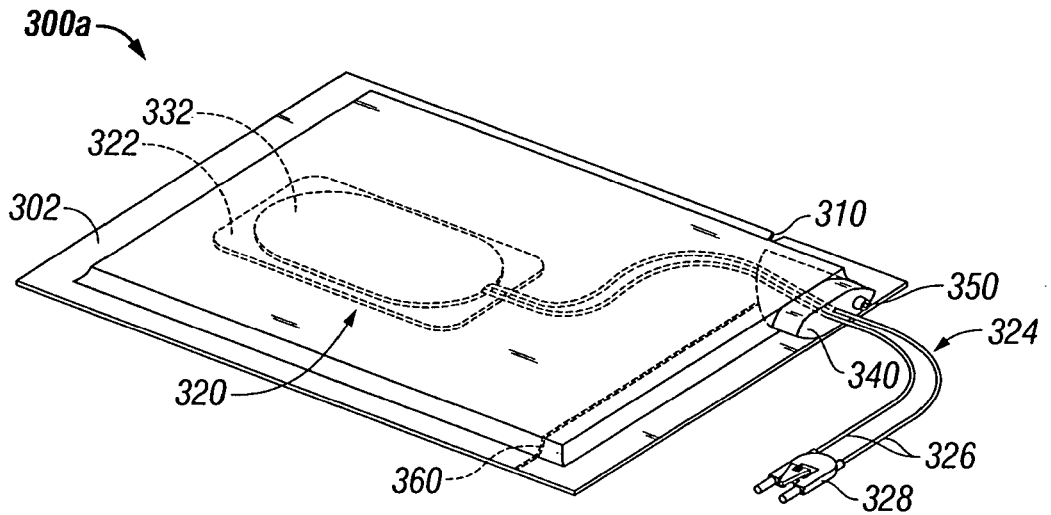
FIG. 3A is a perspective view of another embodiment of the electrode package of FIG. 3.
Figure 3B:
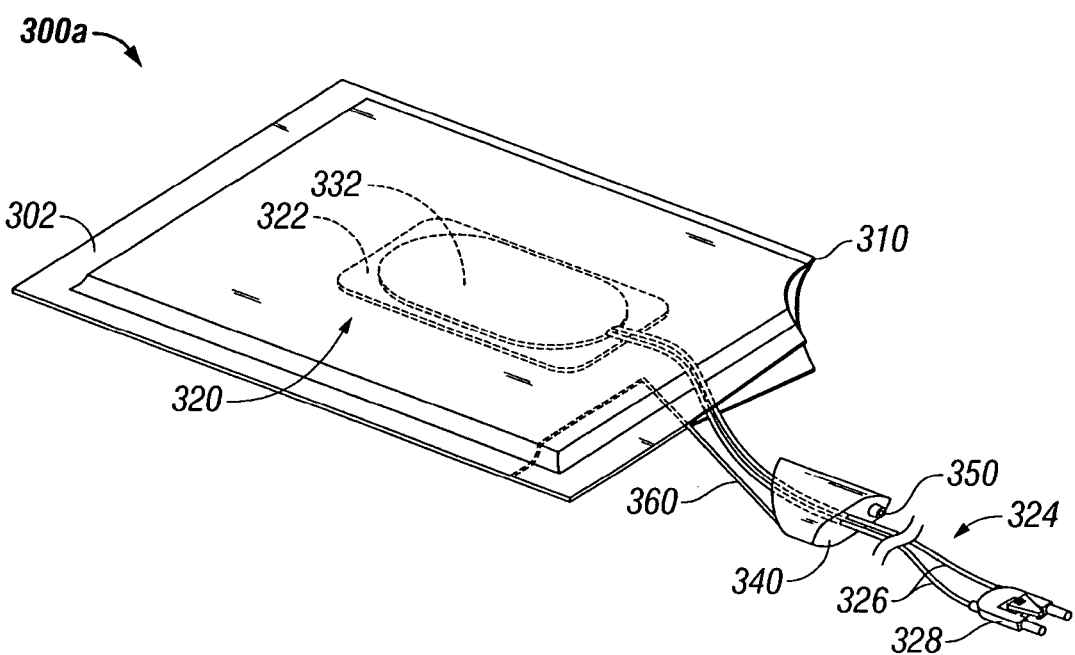
FIG. 3B is a perspective view of the electrode package of FIG. 3A, wherein the electrode package is partially open.

FIGS. 3A and 3B illustrate another embodiment of the electrode package of FIG. 3 and is generally referenced by numeral 300a. Similar to the previous embodiment illustrated in FIG. 3, the electrode package 300a of the present embodiment includes an electrode pouch 302, an electrode 320 and a shell 340 having a check valve 350. Here, however, shell 340 is disposed near a corner of pouch 302 and a tear string 360 is connected to shell 340 and pouch 302.

To remove electrode 320 from electrode pouch 302 in this embodiment, one may tear electrode pouch 302 along notch 310 (disposed near a corner of electrode pouch 302), which detaches shell 340 from electrode pouch 302. When shell 340 is detached from electrode pouch 302, only a relatively small portion of electrode pouch 302 remains attached to shell 340. FIG. 3B illustrates electrode pouch 302 which has been partially opened and with shell 340 exposed. Continued pulling of shell 340 away from electrode pouch 302 causes tear string 360 to rip open the remainder of the top portion of electrode pouch 302, thereby permitting electrodes 320 to be removed therefrom. When fully removed from electrode pouch 302, shell 340 includes a relatively small portion of electrode pouch 302 attached thereto and one end of tear string 360 extending therefrom (which can be removed by various methods if desired).

Figure 4A:
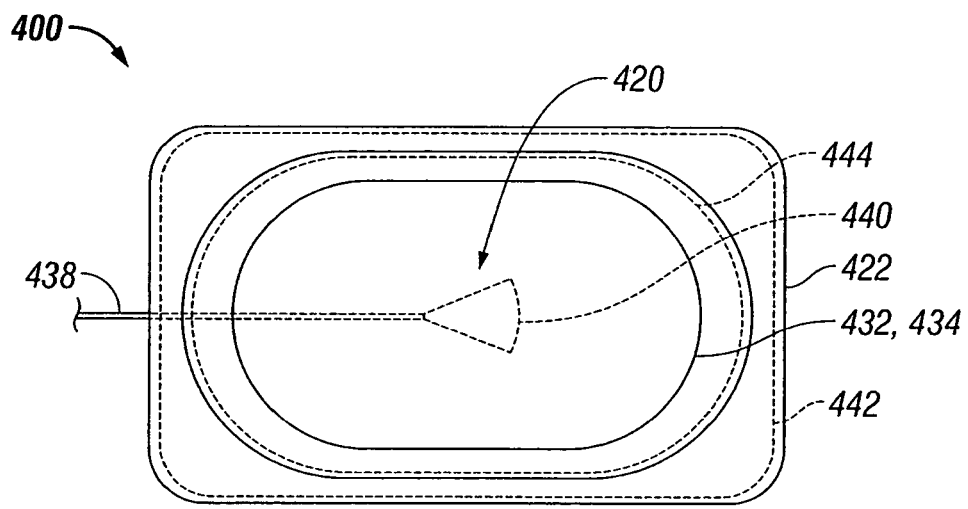
FIG. 4A is a top view of a fourth embodiment of an electrode package in accordance with the present disclosure.
Figure 4B:
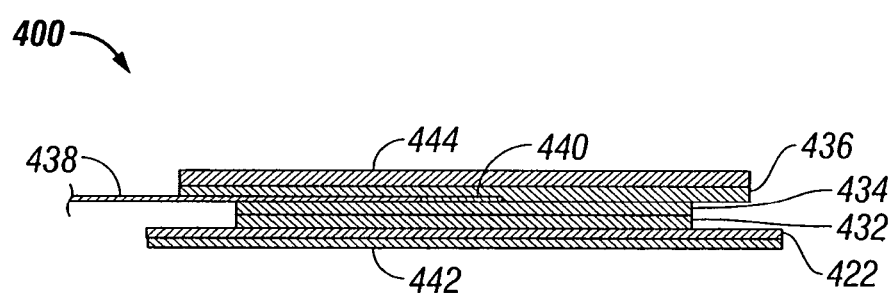
FIG. 4B is a cross-sectional view of the electrode package of FIG. 4.

A fourth embodiment of an electrode package is illustrated in FIGS. 4A and 4B and is generally referenced by numeral 400. The electrode package 400 depicted in this embodiment limits the diffusion of moisture from conductive gel 432 into the air, thus maintaining the moisture content of the conductive gel 432. This embodiment includes an electrode 420, which includes a protective liner 422, conductive gel 432, a conductive substrate 434, an insulating layer 436, lead wires 438, an electrode pad 440, a first membrane 442 and a second membrane 444.

With continued reference to FIGS. 4A and 4B, lead wires 438 connect the electrode pad 440 to a plug portion (not shown). The conductive gel 432 may be directly or indirectly applied to the electrode pad 440 to help the electrode pad 440 adhere to a patient. The conductive substrate 434 may be disposed between the electrode pad 440 and the conductive gel 432, as illustrated in FIG. 4B. The protective liner 422 is disposed adjacent the conductive gel 432 (opposite the insulating layer 436) and it protects the conductive gel 432 prior to use of the electrode 420. The first membrane 442, which is generally gas-impermeable, is integrated into (or connected to) the protective layer 422 to restrict the diffusion of moisture from the bottom surface of the conductive gel 432.

The second membrane 444 is generally gas-impermeable and it limits the diffusion of moisture from the top surface of the conductive gel 432. The second membrane 444 may be integral with or connected to the insulating layer 436, or alternatively, the second membrane 444 may be integral with or connected to the conductive substrate 434. Thus, the overall moisture content of the conductive gel 432 remains sufficient for an extended period of time, due in part to the first membrane 442 limiting the amount of moisture loss from the bottom surface of the conductive gel 432 and the second membrane 444 limiting the amount of moisture loss from the top surface of the conductive gel 432. The first membrane 442 and the second membrane 444 may be made from various materials, including a metal foil.

Figure 5A:
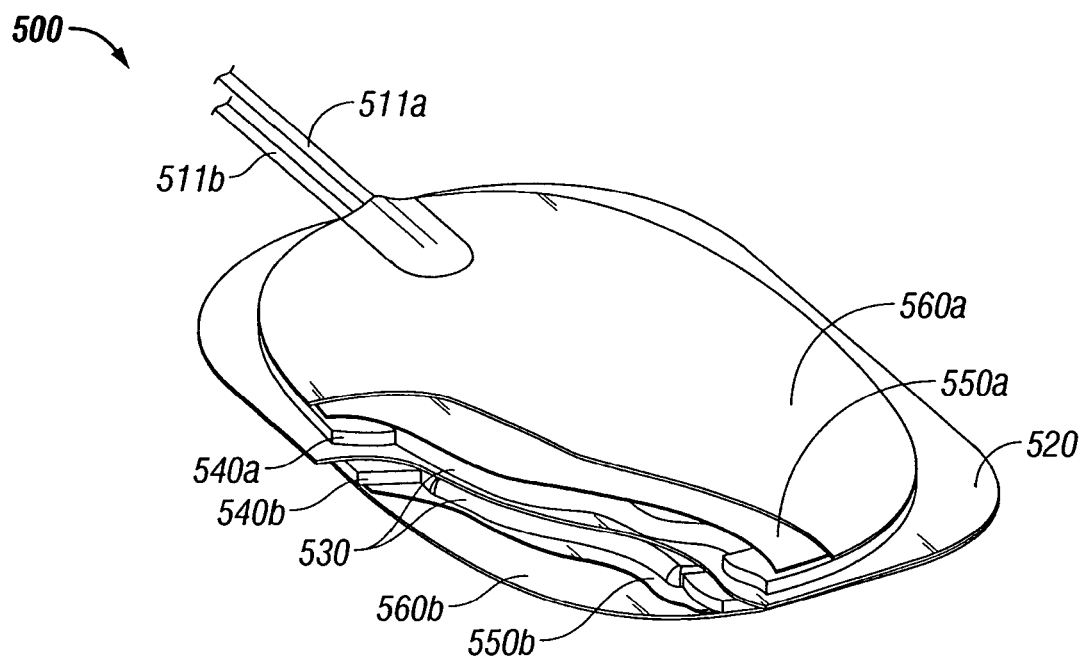
FIG. 5A is a perspective view of a fifth embodiment of an electrode package in accordance with the present disclosure.
Figure 5B:
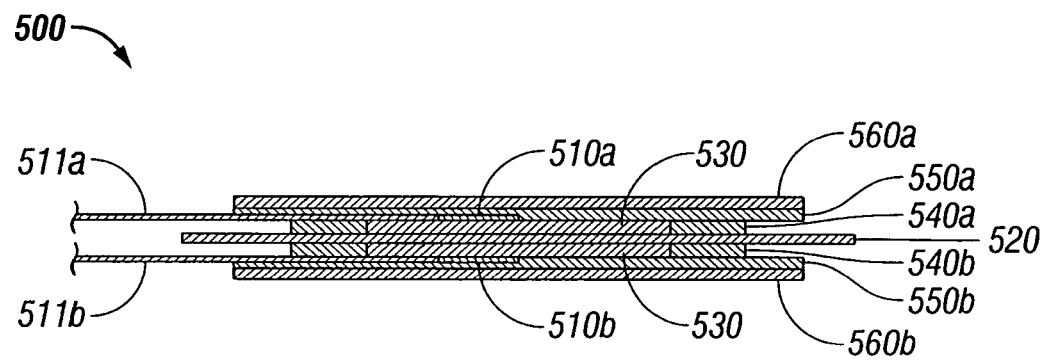
FIG. 5B is a cross-sectional view of the electrode package of FIG. 5.

A fifth embodiment of an electrode package is illustrated in FIGS. 5A and 5B and is generally referenced by numeral 500. The electrode package 500 of this embodiment of the present disclosure includes a first electrode 510a and a second electrode 510b (FIG. 5B), a protective liner 520, conductive gel 530, adhesive rings 540a and 540b, conductive layers 550a and 550b and gas-impermeable membranes 560a and 560b. Lead wires 511a and 511b extend from the electrodes 510a and 510b, respectively, to a plug portion (not shown) for connection to a medical device (not shown), such as a defibrillator.

This embodiment of the disclosure restricts the diffusion of moisture from the conductive gel 530 to the air within the interior of the electrode packaging. Generally, two electrodes 510a and 510b are releasably adhered to either side of the protective liner 520. The protective liner 520 generally protects the conductive gel 530 prior to use of the electrodes 510a, 510b and is removed (e.g., the electrodes 510a, 510b are peeled from the protective liner 520) before the electrodes 510a, 510b are applied to a patient.

In the embodiment illustrated in FIGS. 5A and 5B, adhesive rings 540a and 540b are disposed around the conductive gel 530. The adhesive rings 540a and 540b may help prevent the conductive gel 530 from spreading radially and they may also provide a surface to which the conductive layers 550a and 550b may adhere. The conductive layers 550a and 550b may be disposed of a generally gas-impermeable material, such as aluminum, and may help mitigate the moisture loss from the conductive gel 530. Other materials from which the conductive layers 550a, 550b may be made include various metal foils, such as tin, silver, or aluminum.

The gas-impermeable membranes 560a, 560b are integrated with or are disposed adjacent the conductive layers 550a, 550b, respectively. These gas-impermeable membranes 560a, 560b help impede the diffusion of moisture from the conductive gel 530. Additionally, at least one of the gas-impermeable membranes 560a, 560b may be made of foam or a foam-type material. Other materials from which the gas-impermeable membranes 560a, 560b may be made include a metal foil, such as tin, silver, or aluminum.

It is envisioned that because the design of the electrode package 500 of the fifth embodiment minimizes moisture loss from the conductive gel 530, the electrode package 500 may or may not be stored in a secondary gas-impermeable pouch (not shown) or gas-permeable pouch (not shown). A protective packaging (not shown) may be employed to protect the structural integrity of the electrode package 500 during packaging, transport, storage, and the like.

Figure 6:
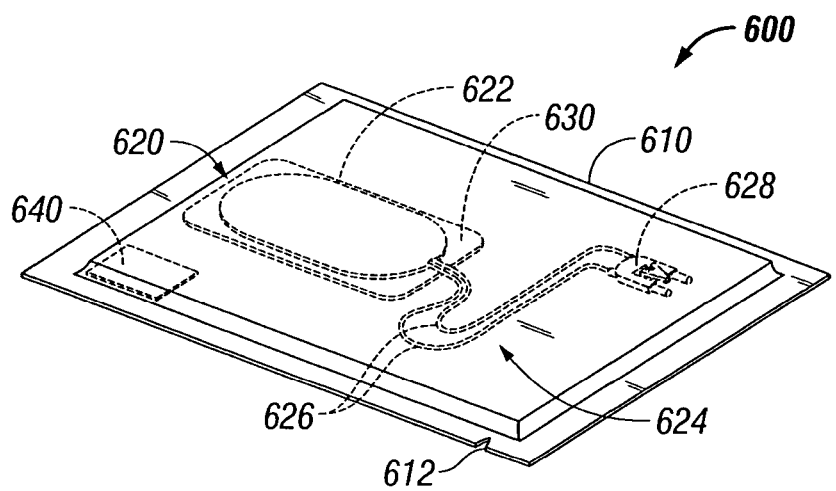
FIG. 6 is a top view of a sixth embodiment of an electrode package in accordance with the present disclosure.

A sixth embodiment of an electrode package is illustrated in FIG. 6 and is generally referenced by numeral 600. The electrode package 600 according to this embodiment includes an electrode pouch 610, an electrode 620 and a sacrificial source of moisture 640.

In this embodiment of the electrode package 600, the electrode pouch 610 may be either generally gas-impermeable or gas-permeable. Within the electrode pouch 610 is an electrode 620 and a sacrificial source of moisture 640. The electrode 620 includes an electrode pad 622 adhered to a cover 630 via conductive gel (not shown), and an electrode connector 624, which includes lead wires 626 and a plug portion 628. It is envisioned that the electrode pouch 610 is re-sealable. In such an embodiment, the electrode 620 can be tested prior to use and then placed back into the electrode pouch 610 and re-sealed.

The sacrificial source of moisture 640 is generally located within the electrode pouch 610 and may be in the form of a solid hydrogel with high water content, for example. Additionally, the sacrificial source of moisture 640 may be attached to the interior of the electrode pouch 610 such that it remains inside the electrode pouch 610 when the electrode 620 is removed.

Generally, in electrode pouch 610, moisture may diffuse over time from its interior to the exterior of the electrode pouch 610. This movement of moisture would typically require moisture from the conductive gel to diffuse into the air within the electrode pouch 610 to maintain chemical equilibrium. The presence of the sacrificial source of moisture 640 provides an additional source of moisture, which will diffuse into the air within the electrode pouch 610 to help maintain the chemical balance. The degree and duration of time of release of the sacrificial source of moisture 640 may be selectively controlled with the proper choice of source materials. The sacrificial source of moisture 640 thereby reduces the amount of moisture that diffuses from the conductive gel. Therefore, this embodiment of the electrode package 600 reduces the diffusion of moisture from the conductive gel to the air within the interior of the electrode pouch 610. Consequently, the moisture content of the conductive gel is maintained at a desirable level for a longer period of time than it would be without the use of the sacrificial source of moisture 640.

In use, a clinician may open the electrode pouch 610 (possibly facilitated by a notch 612), test the electrode 620 for compatibility, and then either remove the electrode 620 from the electrode pouch 610 for use, or place the electrode connector 624 back into the electrode pouch 610, and possibly re-seal the electrode pouch 610, for later use.

Another aspect of the present disclosure is illustrated in FIGS. 7-9. These figures illustrate various embodiments of storing lead wires 126 within an electrode pouch (not shown in FIGS. 7-9). Generally, in these embodiments, a longer quantity of lead wires 126 may be stored within electrode pouch while reducing the possibly of lead wires 126 becoming tangled or otherwise snarled. In these various embodiments, lead wires 126 are extensible, thus facilitating their use and the ability of plug portion 128 to be plugged into a medical device, while reducing the possibility of lead wires 126 becoming tangled either within or outside of the electrode pouch.

A first embodiment of extensible lead wires 126 is shown in FIGS. 7A-7D. In this embodiment, a retaining structure or tube 700 is employed to maintain lead wires 126 in a desired orientation. As seen in FIG. 7C, the cross-section of a tube 700a is generally circular and includes a slot 702 therethrough. In the embodiment shown in FIG. 7D, the cross-section of a tube 700b, which does not include a slot, is illustrated.

With reference to the embodiment of tube 700a illustrated in FIG. 7C, slot 702 allows tube 700 to be placed over lead wires 126. In the embodiment of tube 700b illustrated in FIG. 7D, it is envisioned that lead wires 126 are threaded through tube 700b and then subsequently connected to electrodes 120 and/or plug portion 128.

Although tube 700 is illustrated in FIG. 7C (tube 700a) and 7D (tube 700b) as having a circular cross-section, it is envisioned that the cross-section of tube 700 may be any regular or irregular shape, such that tube 700 allows at least a portion of lead wires 126 to slide therethrough. It is also envisioned that tube 700 is formed around the lead wires 126.

With reference to FIG. 7A, lead wires 126 are shown in a relatively large loop (which fits into an electrode pouch) and passing through tube 700. Lead wires 126 may either be threaded through tube 700b, for example. Additionally or alternatively, tube 700a, for example, may be placed over looped lead wires 126. From these configurations, lead wires 126 are able to be pulled away from electrodes 120. In an embodiment of the disclosure, tube 700 is secured to the interior of the electrode pouch.

It is envisioned that tube 700 of the present embodiment is used in combination with an embodiment of FIGS. 1-6 or independently thereof. As such, lead wires 126 may be pulled either while electrodes 120 are within electrode pouch and/or after electrodes 120 have been removed from electrode pouch. As can be appreciated, lead wires 126 may take up a smaller amount of space when lead wires 126 pass through tube 700. For example, as shown in FIGS. 7A and 7B, a first diameter d1 of loop of lead wires 126 when not extended may be about 5 inches and a second diameter d2 of loop of lead wires 126 when extended (or partially extended) may be about 1 inch. It is contemplated that tube 700 may be removed from lead wires 126 or alternatively, tube 700 may remain on lead wires 126 after electrodes 120 have been removed from electrode pouch.

A second embodiment of extensible lead wires 126 is shown in FIGS. 8A and 8B. In this embodiment, a strap 800 is employed to maintain lead wires 126 in a desired orientation. Strap 800 may include a Velcro® hook and loop fastener and/or a different suitable type of adhesive material for securing strap 800 to itself or to lead wire 126. Strap 800 may also include a non-adhesive material (e.g., a foam-type material) in combination with an adhesive material. In a disclosed embodiment, it is envisioned that the non-adhesive material contacts lead wires 126 and the adhesive material does not come into contact with lead wires 126. In the illustrated embodiment, a loop of lead wires 126 is formed and strap 800 maintains lead wires 126 in position.

According to the present disclosure, it is envisioned that an end of strap 800 is secured to a lead wire 126. It is also envisioned that strap 800 is not secured to either of lead wires 126, i.e., strap 800 attaches to itself. In a contemplated embodiment, strap 800 is loosely secured around lead wires 126, thus allowing at least a portion of lead wires 126 to be pulled therethrough. It is also envisioned that a portion of strap 800 is secured to interior of electrode pouch.

It is envisioned that strap 800 of the present embodiment is used in combination with an embodiment of FIGS. 1-6 or independently thereof. As such, lead wires 126 may be pulled either while electrodes 120 are within electrode pouch (not shown) and/or after electrodes 120 have been removed from electrode pouch. As can be appreciated, lead wires 126 may take up a smaller amount of space when lead wires 126 are secured by strap 800. For example, as shown in FIGS. 8A and 8B, a first effective length L1 of lead wires 126 when not extended may be about 45 inches and a second effective length L2 of lead wires 126 when extended (or partially extended) may be about 80 inches. It is contemplated that strap 800 may be removable from lead wires 126 or alternatively, strap 800 may remain on lead wires 126 (as illustrated in FIG. 8B) after electrodes 120 have been removed from electrode pouch.

Figure 9A:
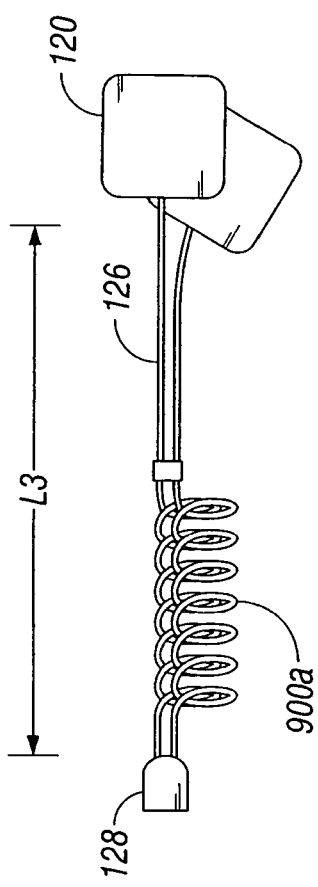
FIG. 9A is a side view of a third embodiment of extensible electrode lead wires in accordance with the present disclosure illustrated in a non-extended manner.
Figure 9B:
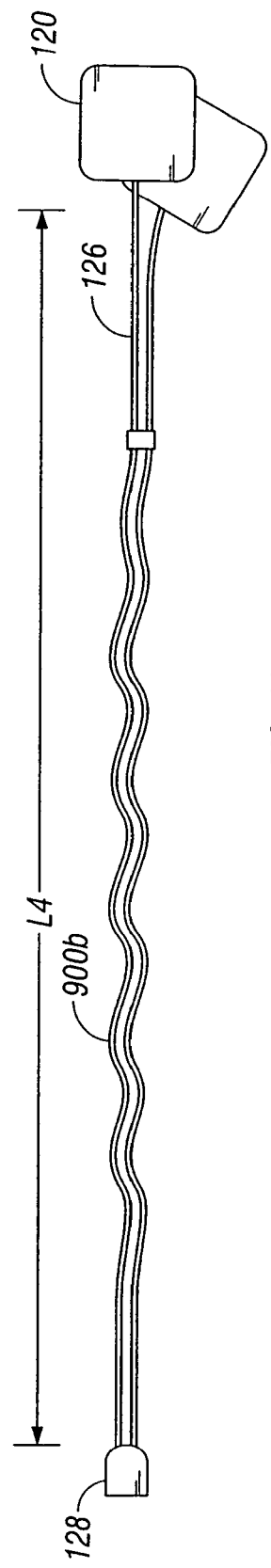
FIG. 9B is a side view of the extensible lead wires of FIG. 9A illustrated in an extended manner.

A third embodiment of extensible lead wires 126 is shown in FIGS. 9A-9B. In this embodiment, lead wires 126 include a coiled section 900a (FIG. 9A). Coiled section 900a maintains lead wires 126 in a desired orientation and minimizes the amount of space necessary to store lead wires 126 (e.g., in an electrode pouch) without lead wires 126 becoming tangled. FIG. 9A illustrates the lead wires 126 having coiled section 900a (similar to a telephone cord) and FIG. 9B illustrates lead wires 126 having an uncoiled section 900b.

It is envisioned that coiled section 900a of the present embodiment is used in combination with an embodiment of FIGS. 1-8 or independently thereof. As such, lead wires 126 may be pulled, resulting in an uncoiled section 900b, either while electrodes 120 are within electrode pouch (not shown) and/or after electrodes 120 have been removed from electrode pouch. As can be appreciated, lead wires 126 may take up a smaller amount of space when lead wires 126 include coiled section 900a.

For example, as shown in FIGS. 9A and 9B, a first effective length L3 of lead wires 126 having coiled section 900a may be about 45 inches and a second effective length L4 of lead wires 126 having uncoiled section 900b (or partially uncoiled) may be about 80 inches. That is, when a user pulls lead wires 126 (e.g., from plug portion 128) which include coiled section 900a, lead wires 126 extend and result in uncoiled section 900b. Further, it is contemplated that releasing lead wires 126 having uncoiled section 900b results in a coiling of lead wires 126, thus re-forming coiled section 900a.

It is to be understood that the foregoing description is merely a disclosure of particular embodiments and is in no way intended to limit the scope of the disclosure. Other possible modifications will be apparent to those skilled in the art and are intended to be within the scope of the present disclosure. For example, it is envisioned that to open an electrode pouch, one may cut it rather than tearing it. It is further envisioned that in the embodiment having a notch on the electrode pouch, there may be a notch (or notches) disposed at both sides of the electrode pouch (illustrated in FIG. 3). Additionally, a perforated line (also illustrated in FIG. 3) may disposed adjacent a notch, or in place of a notch, to facilitate opening the electrode pouch. It is still further envisioned for several of the disclosed embodiments to be used in combination with each other. For example, the electrode packages of the fourth, fifth and sixth embodiments may be used within the electrode pouch of the first, second, third, fourth or fifth embodiments. Other combinations are also anticipated and within the scope of the present disclosure, including the inclusion of a sacrificial source of moisture in any of the embodiments of FIGS. 1-5. Additionally, one or more than one electrode may be present in any of the disclosed embodiments.

What is claimed:

1. An electrode package, comprising:
   a protective liner having first and second opposing surfaces;
   a first conductive layer having first and second opposing surfaces, with a first one of the first and second surfaces disposed over a first one of the first and second surfaces of the protective liner;
   a second conductive layer having first and second opposing surfaces, with a first one of the first and second surfaces disposed over a second one of the first and second surfaces of the protective liner;
   a first generally gas impermeable membrane disposed over a second one of the first and second surfaces of the first conductive layer; and
   a second generally gas impermeable membrane disposed over a second one of the first and second surfaces of the second conductive layer.

2. The electrode package of claim 1 further comprising:
a first conductive gel layer disposed between the first one of the first and second surfaces of the first conductive layer and the first one of the first and second surfaces of the protective liner; and
a second conductive gel layer disposed between the first one of the first and second surfaces of the second conductive layer and the second one of the first and second surfaces of the protective liner.

3. The electrode package of claim 2 further comprising:
a first adhesive ring disposed between a first one of the first and second surfaces of the first conductive layer and the first one of the first and second surfaces of the protective liner; and
a second adhesive ring disposed between a first one of the first and second surfaces of the second conductive layer and the second one of the first and second surfaces of the protective liner.

4. The electrode package of claim 3 wherein the first adhesive ring forms a boundary about the first conductive gel layer and the second adhesive ring forms a boundary about the second conductive gel layer.

5. The electrode package of claim 1, wherein the first and second conductive layers are comprised of a substantially gas impermeable material.

6. The electrode package of claim 5 wherein the first and second conductive layers are comprised of a metal foil.

7. The electrode package of claim 6 wherein the first and second conductive layers are comprised of at least one of tin, silver, or aluminum.

8. The electrode package of claim 1 where the first and second membranes are comprised of a foam-type material.

9. The electrode package of claim 1 where the first and second membranes are comprised of a metal foil.

10. The electrode package of claim 9 where the first and second membranes are comprised of at least one of tin, silver, or aluminum.

11. An electrode packaging system, comprising:
an electrode pouch; and
an electrode package disposed at least partially within the electrode pouch, the electrode package comprising:
a protective liner having first and second opposing surfaces;
a first conductive layer having first and second opposing surfaces, with a first one of the first and second surfaces disposed over a first one of the first and second surfaces of the protective liner;
a second conductive layer having first and second opposing surfaces, with a first one of the first and second surfaces disposed over a second one of the first and second surfaces of the protective liner;
a first generally gas impermeable membrane disposed over a second one of the first and second surfaces of the first conductive layer; and
a second generally gas impermeable membrane disposed over a second one of the first and second surfaces of the second conductive layer.

12. The system of claim 11, wherein the electrode pouch is substantially gas-impermeable.

13. The system of claim 11, further comprising a protective packaging to protect the structural integrity of the electrode package during packaging.

14. The system of claim 11 further comprising:
a first conductive gel layer disposed between a first one of the first and second surfaces of the first conductive layer and a first one of the first and second surfaces of the protective liner; and
a second conductive gel layer disposed between a first one of the first and second surfaces of the second conductive layer and a second one of the first and second surfaces of the protective liner.

15. The system of claim 14 further comprising:
a first adhesive ring disposed between a first one of the first and second surfaces of the first conductive layer and a first one of the first and second surfaces of the protective liner; and
a second adhesive ring disposed between a first one of the first and second surfaces of the second conductive layer and a second one of the first and second surfaces of the protective liner.

16. The system of claim 15 wherein the first adhesive ring forms a boundary about the first conductive gel layer and the second adhesive ring forms a boundary about the second conductive gel layer.

17. The system of claim 11 wherein the first and second conductive layers are comprised of a metal foil.

18. The system of claim 11 where the first and second membranes are comprised of a foam-type material.

19. The system of claim 11 where the first and second membranes are comprised of a metal foil.

20. A method of packaging electrodes, comprising:
providing a protective liner having first and second opposing surfaces;
providing a first conductive layer having first and second opposing surfaces, with a first one of the first and second surfaces disposed over a first one of the first and second surfaces of the protective liner;
providing a second conductive layer having first and second opposing surfaces, with a first one of the first and second surfaces disposed over a second one of the first and second surfaces of the protective liner;
providing a first generally gas impermeable membrane disposed over a second one of the first and second surfaces of the first conductive layer; and
providing a second generally gas impermeable membrane disposed over a second one of the first and second surfaces of the second conductive layer.

* * * * *